United States Patent [19]

Martin

[11] Patent Number: 4,555,522

[45] Date of Patent: Nov. 26, 1985

[54] ANTITHROMBOTIC AND/OR ANTIHYPERTENSIVE COMPOSITIONS

[75] Inventor: Bernard K. Martin, Bagshot, England

[73] Assignee: T & R Chemicals, Inc., Clint, Tex.

[21] Appl. No.: 567,914

[22] Filed: Jan. 3, 1984

[30] Foreign Application Priority Data

Jan. 5, 1983 [GB] United Kingdom ............... 8300102

[51] Int. Cl.$^4$ .................. A61K 31/335; A61K 31/35; A61K 31/34; A61K 31/266
[52] U.S. Cl. .................................. 514/449; 514/517; 514/450; 514/456
[58] Field of Search ............... 424/303, 278, 283, 285; 514/449, 450, 456

[56] References Cited

U.S. PATENT DOCUMENTS

| | | | |
|---|---|---|---|
| 2,968,667 | 1/1961 | Lawlor | 260/456 |
| 3,189,632 | 6/1965 | Horvath et al. | 424/303 |
| 3,311,534 | 3/1967 | Covey et al. | 424/303 |
| 3,803,200 | 4/1974 | Senning et al. | 424/303 |
| 3,836,639 | 9/1974 | Teler et al. | 424/101 |
| 4,327,083 | 4/1982 | Alvarez | 424/162 |
| 4,402,943 | 9/1983 | Thompson | 424/180 |
| 4,402,946 | 9/1983 | Thompson | 424/180 |

FOREIGN PATENT DOCUMENTS

| | | |
|---|---|---|
| 0043274 | 1/1982 | European Pat. Off. . |
| 7612060 | 11/1977 | France . |
| 58-35166 | 3/1983 | Japan ................. 424/303 |
| 58-38214 | 3/1983 | Japan ................. 424/303 |
| 700710 | 12/1953 | United Kingdom . |
| 705078 | 3/1954 | United Kingdom . |
| 2068952 | 8/1981 | United Kingdom . |

OTHER PUBLICATIONS

Chemical Abstracts: 7: 1551, (1913).
Chemical Abstracts: 42: 2355g, (1948).
Chemical Abstracts: 43: 1861g, (1949).
The Merck Index, 9th Ed., Merck & Co., Publisher, No. 5811, (1976).

Primary Examiner—Albert T. Meyers
Assistant Examiner—Joyce L. Morrison
Attorney, Agent, or Firm—Cushman, Darby & Cushman

[57] ABSTRACT

Hypertension and thrombotic conditions in mammals are treated by administration of sulphite, bisulphite or cyclic sulphite ester of a monohydric or polyhydric alcohol.

8 Claims, No Drawings

ANTITHROMBOTIC AND/OR ANTIHYPERTENSIVE COMPOSITIONS

This invention relates to the treatment of hypertension and thrombotic conditions in mammals (especially man) and provides pharmaceutical compositions for use in carrying out such treatment.

A hypertensive condition exists when systolic and/or diastolic blood pressures in a mammal are elevated above their respective normal values even when the mammals body is in a passive or non-excited state. A hypertensive condition is evidenced by simple blood pressure measurements.

A thrombotic condition exists when a mammal has an existing thrombus and/or an incipient thrombus. For present purposes, the term "thrombus" or equivalent includes the subject matter of the term "embolus" unless the context specifically indicates otherwise. Thrombotic conditions or disorders are generally classifiable into venous thromboses and arterial occlusive disorders. An "incipient thrombus" or "incipient thrombotic condition", as such a term is used herein, can exist in a patient who has a predisposed condition for development of a thrombotic condition. For example, diabetes mellitus and hyperlipedemia are conditions which predispose a patient to arterial thromboses. On the other hand, surgery, trauma, and bed rest for example, are conditions which predispose a patient to venous thrombosis. Examples of an existing thrombus or existing thrombotic condition include stroke (such as a cerebral vascular thrombosis), myocardial infarction (coronary artery disease), peripheral vascular disease, need for a cardiac valve replacement, deep venous thrombosis, and pulmonary embolism.

Those skilled in the practice of medicine routinely determine the presence of a thrombotic condition (including an actual or existing thrombus in a patient). Such a condition is determinable for present purposes preferably by state of the art determination techniques; such are known to the art and do not as such constitue a part of the present invention. For example, arterial thrombosis is diagnosable by clinical manifestations, by arteriography, and recently, by an Indium 111 platelet labelling technique (see, for example, "Differential Effects of Two Doses of Aspirin on Platelet Vessel Wall Interaction in vivo", K K Wu et al, *Journal of Clinical Investigation*, August 1981). Also, for example, venous thrombosis is detectable from patient clinical conditions symptomatically perceivable by a skilled medical practitioner, and objectively by various methods, including venography, impedance plethysmography, doppler ultrasound, and the Iodine 125-fibrinogen test; see for example, Kakkar, *Archives of Surgery* 104, page 152 (1972) and J. G. Kellon et al., Journal of Clinical Investigation, Vol. 62, pp 892-895 (1978).

Venous thrombosis of the lower extremities is important because it can cause pulmonary embolism which can be fatal. Heparin and Warfarin are commonly used in clinical medicine for prevention and treatment of deep venous thrombosis and pulmonary embolism.

Platelets play an important part in arterial thrombosis. Drugs that inhibit platelet aggregation are generally regarded as potentially useful for the prophylactic therapy of arterial thrombotic disorders, such as, for example, stroke, myocardial infarction and peripheral vascular disease. Despite the availability of many agents which possess platelet anti-aggregatory properties, only a few are currently under clinical trial (for example, aspirin, dipyridamole and sulphinpyrazone).

Very few agents are known which show effect in both venous thrombosis and arterial occlusive disorders.

An antithrombotic agent is a substance which inhibits formation or development of a thrombus (or an incipient thrombus).

An anticoagulant agent is a substance which inhibits blood clotting and/or prolongs normal blood coagulation time.

An anti-platelet aggregatory agent is a substance which inhibits platelet aggregation.

An anti-platelet aggregatory agent typically does not inhibit blood clotting so is not an anticoagulant agent and so is useful mainly in arterial thrombotic disorder treatment. Similarly, an anticoagulant agent typically does not inhibit platelet aggregation and so is useful mainly in venous thrombotic disorder treatment.

The active agents of the present invention display anticoagulant, anti-platelet aggregatory, and antithrombotic activity and are useful in both arterial thrombosis and venous thrombosis. In addition, these agents display antihypertensive activity.

An antihypertensive agent is a substance which reduces the systolic and/or the diastolic blood pressure in a hypertensive mammal.

The active agents of this invention effectuate blood pressure reduction without apparently causing an objectionable increase in elimination of metal ions, such as sodium, potassium, and calcium, through the kidneys.

As disclosed in European Patent Publication No. 0043274 (published Jan. 6, 1982) and U.S. Pat. Nos. 4327083 (issued Apr. 27, 1982), 4400396 and 4400397 (issued Aug. 23, 1983), 4401654 and 4401655 (issued Aug. 30, 1983), 4402943, 4402946 and 4402982 (issued Sept. 6, 1983), and 4404202 (issued Sept. 17, 1983), discoveries have been made relating to the antithrombotic activity, involving anti-coagulant and/or platelet antiaggregatory activities, and antihypertensive activity of certain sulphites, bisulphites and related compounds.

The present invention is based upon the discovery that when a member of a certain class of pharmaceutical agents is administered to a mammal (including man) antihypertensive and antithrombotic effects are achieved. Administration can be accomplished by oral ingestion, injection, absorption, or otherwise as desired. Injection can be accomplished intravenously, intramuscularly, intraperitoneally, subcutaneously, or otherwise.

The reason why, and the mechanisms by which, the pharmaceutical agents function is not presently known. However, it is theorized (and there is no intent to be bound by theory herein) that these agents, after administration to a mammal undergo a change, probably hydrolysis, resulting in the release of bisulphite and/or sulphite ions. The bisulphite and/or sulphite ions seem to be responsible for the observed beneficial therapeutic effects.

According to one aspect of this invention, there is provided a pharmaceutical composition for use in treating a hypertensive or a thrombotic condition in a mammal, said composition comprising a pharmaceutically acceptable diluent or carrier and, as an active pharmaceutical agent, a sulphite, bisulphite or cyclic sulphite ester of a monohydric or polyhydric alcohol. Preferably, the alcohol has 1 to 6 hydroxy groups.

According to a second aspect of the invention, there is provided, for use in treating a hypertensive or a thrombotic condition in a mammal, a sulphite, bisulphite or cyclic sulphite ester of a monohydric or polyhydric alcohol.

According to a third aspect of the invention, there is provided a method of treating a hypertensive or a thrombotic condition in a patient in need thereof which method comprises administering to the patient an antihypertensive or anti-thrombotic effective amount of a sulphite, bisulphite or cyclic sulphite of a monohydric or polyhydric alcohol.

The esters of the invention can be represented by the following Formula I:

$$Ra-O-\underset{\underset{O}{\|}}{S}-O-Rb \qquad \text{(Formula I)}$$

wherein

Ra represents a residue obtained by removal of an hydroxyl group from a monohydric or polyhydric alcohol and which, in the case of a polyhydric alcohol, can have each of one or more other hydroxyl groups replaced by $$-O-\underset{\underset{O}{\|}}{S}-ORb;$$

each Rb independently represents hydrogen or a residue obtained by removal of an hydroxyl group from a monohydric or polyhydric alcohol and which, in the case of a polyhydric alcohol, can have each of one or more other hydroxyl groups replaced by $$-O-\underset{\underset{O}{\|}}{S}-ORb;$$

or

Ra and Rb together represent a residue obtained by removal of two hydroxyl groups from a polyhydric alcohol and which, in the case of a polyhydric alcohol having more than three hydroxyl groups, can have each of one or more other hydroxyl groups replaced by $$-O-\underset{\underset{O}{\|}}{S}-ORb.$$

Various presently preferred classes of such sulphite esters are represented by the following generic formulae with their accompanying definitions:

(1) $R_1-O-\underset{\underset{O}{\|}}{S}-O-R_2$      (Formula IA)

(2) $R_4-\underset{}{C}\underset{}{\overset{(CH_2)_n-O}{\diagup}}\underset{(CH_2)_m-O}{\diagdown}S=O$      (Formula IB)

(3) $YO-\underset{\underset{O}{\|}}{\overset{O}{S}}-O-CH_2-\left(\underset{\underset{H}{|}}{\overset{R_5}{C}}\right)_k CH_2-O-\underset{\underset{O}{\|}}{\overset{O}{S}}-OY$      (Formula IC)

(4) Formula ID (structure shown)

(5) Formula IE (structure shown)

(6) $(CH_3)_3N^+-(CH_2)_5-O-\underset{\underset{O}{\|}}{S}-O$ where:

$R_1$ represents $C_1$-$C_{10}$ alkyl, or $C_1$-$C_{10}$ hydroxyalkyl having a number of hydroxyl substituents from 1 to a value equal to the number of carbon atoms in the hydroxyalkyl group, $R_2$ represents hydrogen, $C_1$-$C_{10}$ alkyl, or $C_1$-$C_{10}$ hydroxyalkyl having a number of hydroxyl substituents from 1 to a value equal to the number of carbon atom in the hydroxyalkyl group;

$R_3$ represents hydrogen, hydroxymethyl, methyl, or ethyl;

$R_4$ represents hydrogen, hydroxymethyl, methyl, ethyl, $-CH-O-\underset{\underset{O}{\|}}{S}-OH$, or $\underset{CH_2-O}{\overset{-CH-O}{\diagup}}S=O$, or $R_3-\underset{|}{\overset{|}{C}}-R_4$ together represent $O=S\underset{O-CH_2}{\overset{O-CH_2}{\diagup}}C$;

each $R_5$ independently represents hydroxyl or $$-O-\underset{\underset{O}{\|}}{S}-O-Y;$$

Y represents hydrogen, hydroxymethyl, methyl, ethyl, or $-(CH_2)_tN(CH_3)_3$ k represents an integer of from 1 to 5 inclusive;

l represents an integer of from 1 to 4 inclusive; and m and n independently represent 0, 1 or 2 provided that the sum of m and n is 1 or 2;

t represents 1, 2 or 3.

In the case of the esters of Formula IA, it is preferred that the alkyl moieties represented by $R_1$ and $R_2$ have 1 to 6 carbon atoms, especially 1 to 4 carbon atoms. Examples of the esters of Formula IA are dimethylsulphite and diethylsulphite.

In the case of the esters of Formula IB, one preferred subclass is that in which m represents 0, n represents 1, $R_3$ represents hydrogen, and $R_4$ represents hydroxymethyl, methyl,

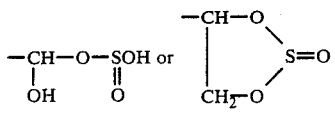

Examples of said subclass are glyceryl-1:2sulphite, propan-1:2-diol sulphite, and erythritol disulphite.

Another preferred subclass of the esters of Formula IB are those compounds in which m represents 1, n represents 1, and $R_3$ and $R_4$ each represent hydroxymethyl or

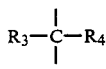

together represents

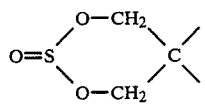

The compounds of said subclass are the mono- and disulphites of pentaerythritol.

In the case of the esters of Formula IC, it is preferred that k represents 4 and/or that $R_5$ represents hydroxyl or especially,

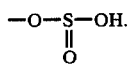

Examples of said subclass are the bisulphite esters of linear sugar alcohols such as mannitol and sorbitol.

A preferred subclass of the esters of Formula ID are those in which l represents 4 and/or $R_5$ represents hydroxy or, especially,

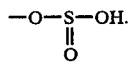

Examples of said subclass are the bisulphite esters of inositol.

In the case of the esters of Formula IE, it is preferred that t represents 1 and/or $R_5$ represents hydroxy or, especially,

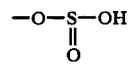

and/or Y represents 0 hydrogen. The esters can be in the form of a pharmacologically acceptable salt, especially a sodium, potassium, ammonium, calcium or magnesium salt (i.e. one or more of the

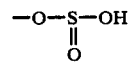

groups can be replaced by

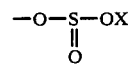

where X represents said cation). Examples of said subclass are the bisulphites of isosorbide.

A preferred subclass of the esters of Formula IF are those in which Y represents

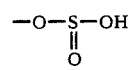

and/or t represents 2.

The dose rate for effective treatment of hypertension or thrombotic condition is variable, being dependent upon such things as the particular agent used, the mammalian species undergoing administration, the time within which an effect is to be observed, and the like. In general, the effects observed are dose related with small doses generally requiring more time before an effect is observed. Typically effects are observable within rates of from about 0.1 to 100, usually 1 to 50 milligrams per kilogram of body weight, though smaller and larger (provided toxic or undesirable side effects are not observed) are within the scope of this invention. Unit doses of the esters usually will contain from about 0.1 to about 1000 mg, preferably about 50 to about 500 mg.

The term "unit dosage form" is used herein to mean a single or multiple dose form containing a quantity of the active ingredient in admixture with or otherwise in association with the diluent or carrier, said quantity being such that one or more predetermined units are normally required for a single therapeutic administration. In the case of multiple dose forms such as liquids or scored tablets, said predetermined unit will be one fraction, such as a 5 ml (teaspoon) quantity of a liquid or a half or quarter of a scored tablet, of the multiple dose form.

In order to be suitable for use in a pharmaceutical composition of this invention, a sulphite ester should be acceptable for pharmaceutical use and have the ability, after administration, to produce antihypertensive and antithrombotic effects.

In the composition aspect of the invention, the compositions are prepared in manner known per se in the pharmaceutical art and usually comprise at least one ester of the invention in admixture or otherwise in association with a pharmaceutically acceptable carrier or diluent therefor. For making the formulations, the active ingredient usually will be mixed with a carrier, or diluted by a diluent, or enclosed or encapsulated in a capsule, sachet, cachet, paper or other container. A carrier or diluent may be solid, semi-solid or liquid material which serves as a vehicle, excipient or medium for the active ingredient. Suitable carrier and diluents are well known per se.

The compositions of this invention may be adapted for enteral or parenteral use and may be administered to the patient in the form of tablets, capsules, suppositories, solutions, suspensions and the like. In the specific examples included hereinafter illustrative examples of suitable pharmaceutical compostions are described.

Unless such contains unreacted hydroxyl groups, it is now believed that sulphite and bisulphite compounds of this invention are poorly soluble in water. Similarly the sulphite esters appear to exhibit different rates of hydrolysis with hydrolysis releasing into water solution or into mammalian body tissue sulphite and/or bisulphite ions. In a substantially pure form, such sulphite esters are apparently stable indefinitely. The sulphite esters as a class appear to have generally long lasting pharmaceutical effects, apparently, it is theorized, whether administered orally or by injection, for example. It is preferred that the sulphite esters are administered orally. When insoluble sulphites are injected, they must, of course, be injected intramuscularly.

One advantage of the esters of the present invention appears to be that their use minimises the amount of inorganic sulphite or bisulphite compounds which would otherwise have to be administered in order to achieve an equivalent effective level of therapeutic effectiveness.

Another advantage appears to be seen in a comparison to other active agents, such as the inorganic and organic sulphite or bisulphite salts. When one of said salts is administered, oxidation to sulphate appears more likely to occur in the mucosal cells of the gut, and also in the course of the first pass of such a compound through the liver, than is the case with the agents of this invention. Thus, a variable and potentially high percentage of the given dose is destroyed with said salts so that only a relatively small amount of the sulphite or bisulphite ions administered orally may reach the site of action in the body. In theoretical contrast to this low bioavailability of sulphite from these salts, the use of the present sulphite esters avoids these two destructive processes and gives rise to a much higher and perhaps more uniform bioavailability for the present pharmaceutical agents.

Although as above indicated the precise mechanisms which occur are not now fully known, it is theorized that the sulphite esters may undergo enzymatic hydrolysis in the body, so that the rate of formation of sulphite ions may vary. This offers the advantage not only of a more sustained and prolonged concentration of the active component, but also of an avoidance of a peak concentration of ions as encountered with the use of simple salts. It is an important advantage of the present invention that the inclusion of two or more different sulphite esters in a composition, each such ester having a different hydrolysis rate, enables a uniform sulphite ion production to take place over extended periods in the body.

Within the entire class of pharmaceutical agents of the invention, a presently preferred sub-group of esters are those derived from mono-, di-, tri-, tetra-, penta-, and hexahydric alcohols. Because sulphite esters are derived from a divalent sulphite radical, they are necessarily more complex than, for example, nitrate esters, and there is a greater range of possibilities in the structure of the products which may be formed when a mono or polyhydric alcohol is used to form a sulphite ester for incorporation in a composition of this invention.

The following are examples of various sulphite esters which can be formulated into a composition with a carrier substance, e.g. purified water, in accordance with this invention.

EXAMPLE 1

Dimethyl sulphite and diethyl sulphite are successively prepared by esterifying 2 moles of each respective alkanol with 1 mole of thionyl chloride. The diethyl ester is a colourless liquid (b.p. 159°) with an aromatic odour, believed to have the following formula:

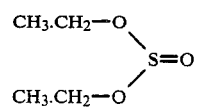

A composition based on this compound, e.g. an aqueous suspension having a concentration in the range from 0.5 to 2.5 millimolar, is effective in the treatment of thrombotic and hypertensive disorders in rats. It is theorized to be activated in vivo by virtue of its conversion to sulphite ions.

The analogous esters of higher alcohols when used, e.g. propyl, butyl or amyl, provide antithrombotic and antihypertensive effects. However, with these esters of higher alcohols, the sulphite content of the ester on a molecular weight basis becomes progressively less and the required dose appears to increase as a consequence.

EXAMPLE 2

The sulphite ester of propylene glycol, i.e. propan-1:2-diol sulphite, is produced by reaction with thionyl chloride and, it is believed, has the following formula:

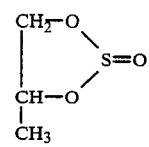

EXAMPLE 3

A mixture of sulphite esters of glycerol is obtained by reaction of glycerol with thionyl chloride. The simplest ester is glyceryl-1:2-sulphite, which can react further to give more complex structures, and has the formula:

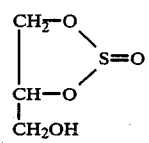

The use of glyceraldehyde instead of glycerol as the reactant with thionyl chloride provides a sulphite ester having the ability to form an additional complex with sodium bisulphite; the complex having the formula:

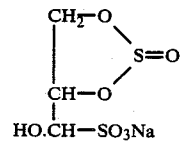

EXAMPLE 4

Erythritol disulphite is produced by reaction of the corresponding tetrahydric alcohol with thionyl chloride and has the formula:

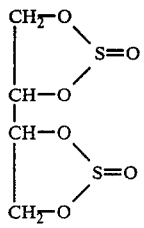

EXAMPLE 5

D-Fructofuranose-1,3,4,6-disulphite also is prepared by reaction of the corresponding alcohol with thionyl chloride and is believed to be similar in chemical structure to the corresponding tetranicotinate (Nicofuranose).

EXAMPLE 6

The mono- and di-sulphite esters of 2-2-di(hydroxymethyl)propan-1:3-diol are produced by reaction of the corresponding pentaerythritol with thionyl chloride. The sulphites have the respective formulae:

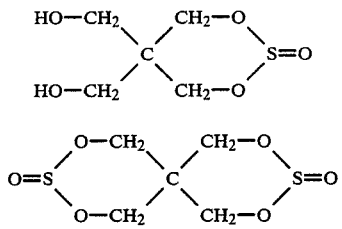

Whereas the corresponding tetranitrate ester is known and is in use, stearic effects of the larger sulphite radical may render difficult the formation of the disulphite ester.

EXAMPLE 7

By analogy with inositol hexanicotinate and mannitol hexanitrate, the corresponding sulphite esters are believed to exist as trisulphites involving a cyclic sulphite structure, or, more advantageously, involving hexabisulphite esters.

Mixed sulphite esters of inositol, mannitol and sorbitol are produced by reaction of these sugar alcohols with thionyl chloride.

The sulphite esters of sorbitol mono- and di-anhydrides with sulphurous acid also comprise sulphite-generating precursors of this invention, such as the di-ester of 1,4:3,6-dianhydrosorbitol (isosorbide diester).

EXAMPLE 8

The choline ester is of particular interest, even though it has a relatively low sulphite content in comparison with the simple compounds, because it appears to be both a salt and internal salt (zwitterion). It is prepared by reaction of thionyl chloride with choline.

EXAMPLE 9

Evaluation of anti-platelet aggregatory effectiveness

In order to evaluate the effectiveness of diethyl sulphite as an anti-platelet aggregatory agent the following experiments are carried out.

(A) In vitro Platelet-rich plasma (PRP) is prepared from a rabbit and the IC50 value is determined according to the method of Born, "Nature", 194, 927–929 (1962). The IC50 is the estimated concentration of the agent necessary to inhibit 50 percent of the platelet aggregation. The data tabulated below is obtained.

| STIMULUS | IC50 of diethyl sulphite |
| --- | --- |
| Arachidonic acid | 6.25 millimolar |
| U-46619* | 11.0 millimolar |
| Adenosine diphosphate (ADP) | 35.0 millimolar |

*U-46619 is a prostaglandin-endoperoxide-$H_2$ analogue, namely 15-hydroxy-11,9-epoxymethano=prosta-5Z, 13E-enoic acid.

(B) Ex vivo A rabbit weighing 3.06 kg is injected with 219 mg of diethyl sulphite to give a concentration of about 10 millimolar diethyl sulphite in the blood. After 10 minutes, a blood sample is withdrawn and the percent inhibition of platelet aggregation, as compared to a blood sample taken before injection, is determined. The data shown below is obtained:

| STIMULUS | PERCENT INHIBITION |
| --- | --- |
| Arachidonic acid | 0 |
| U-46619 | 12 |
| ADP | 29 |

When each of the compounds of Examples 2 to 8 respectively is evaluated for anti-platelet aggregatory activity by the procedure of Example 9A, such is found to possess good activity.

EXAMPLE 10

Evaluation of anticoagulant effectiveness

In order to evaluate the effectiveness of sulphite esters as anticoagulant agents, the following experiment is carried out.

The compound of each of Examples 1–8 is dissolved in ethanol and then each is added to human and rabbit plasma in vitro. All compounds are found to prolong PT and PTT at a concentration of 0.5 mg/ml of compound and the effects are found to be dose related.

The evaluation procedure used as described in a standard textbook entitled "Human Blood Coagulation Haemostasis and Thrombosis" edited by Rosemary Biggs, published by Blackwell Scientific Publications, Oxford, England (2nd Edition), pages 670–705 (1976).

EXAMPLE 11

Evolution of antihypertensive effectiveness

In order to evaluate the effectiveness of sulphite esters as anticoagulant agents, the following experiment is carried out.

A strain of rat is selected with a blood pressure higher than that normally present in laboratory rats. This hypertension is genetically determined and develops as the rats age. Ideally, older rats showing more pronounced hypertension are used. The rats are weighed and then anaesthetised with urethane (1500 mg/kg i.p.). This anaesthetic has a long duration of action (more than 3 hours) and little effect on the mechanism of homeostasis. The rates are prepared for recording blood pressure directly from a carotid artery. The artery is cannulated with a fine nylon catheter connected to a pressure transducer filled with normal saline containing sufficient heparin to prevent coagulation. The blood pressure (phasic and mean) is recorded on a recorder using appropriate preamplifiers and conditioning units. The trachea is cannulated to avoid respiratory problems during prolonged anaesthesia and the body temperature of the rats is maintained constant by means of a heated pad under the rat controlled by a rectal sensor.

The test compounds are administered by intraperitoneal injection. This route is selected in preference to the oral route which gives poor and irregular absorption in anaesthetised preparations and also in preference to the intravenous route which cannot be used for insoluble materials. The intraperitoneal route is also preferred because it resembles the oral route in that test materials pass primarily to the liver after absorption. Wherever possible substances are given as aqueous solutions but otherwise as emulsions stabilised with TWEEN 80 or as suspensions in methyl cellulose.

Each of the compounds of Examples 1-8 respectively, demonstrates blood pressure lowering effects in this test.

EXAMPLE 12

Compositions

The following illustrate the kinds of formulations which can be used to provide the means for carrying out the invention.

| A - CREAM | |
|---|---|
| | % w/v |
| Diethyl sulphite | 5.0 |
| Cetomacrogol | 1.0 |
| Cetostearyl alcohol | 5.0 |
| Soft paraffin | 15.0 |
| Liquid paraffin | 7.0 |
| Glycerin | 5.0 |
| Water to | 100.0 |

The ingredients are made into the desired formulation using standard procedures.

| B - CREAM | |
|---|---|
| | % w/v |
| Isosorbide sulphite | 10.0 |
| Cream base to | 100.0 |

The cream base is made up from the same ingredients as are used for the non-active component of Example A. Another optional feature is the incorporation of dimethyl sulphoxide (DMSO), typically in up to 10 w/v in order to facilitate penetration of the formulations into the skin.

| C - SOFT GELATIN CAPSULES | |
|---|---|
| Diethyl sulphite | 250 mg |

The material is distributed into soft gelatin capsules which, when filled, are then sealed.

| D - HARD GELATIN CAPSULES | |
|---|---|
| Isosorbide sulphite | 200 mg |
| Corn starch | 25 mg |

The compounds are thoroughly mixed and then distributed into hard gelatin capsules which, when filled, are then each sealed.

| E - TABLETS | |
|---|---|
| Isosorbide sulphite | 200 mg |
| Lactose | 50 mg |
| Corn starch | 25 mg |
| Magnesium stearate | 2 mg |
| Talc | 2 mg |

The starting powders are mixed together thoroughly and subjected to the "slugging" process. The product "slugs" are broken into small granules which are then admixed (on a 100 weight percent total weight basis) with a further 5 weight percent of corn starch. The resulting mixture is metered into dose units which are compressed into tablets.

| F - INJECTABLE SOLUTION | |
|---|---|
| Propan-1,2-sulphite | 300 mg |
| Propylene-glycol | 100 mg |
| Ethyl alcohol | 100 mg |
| Water for injection to | 1 ml |

The solution is produced by sterilizing all containers and placing the product solution in a sealed glass ampoule.

| S - SUPPOSITORY | |
|---|---|
| | mg/suppository |
| Diethyl Sulphite | 200 |
| Oil of Theobroma (Cocoa butter) | 800 |

The diethyl sulphite and molten oil of theobroma are mixed at 45° C. to form a smooth paste which is poured into moulds each of nominal 1 g capacity to produce suppositories.

I claim:

1. A pharmaceutical composition in unit dosage form for use in treating a hypertensive or a thrombotic condition in a mammal, said composition comprising a pharmaceutically acceptable diluent or carrier and, as an active pharmaceutical agent, from 50 to 1,000 mg per unit dose of a sulphite or bisulphite ester having:

(A) the Formula IA:

(Formula IA)

$$R_1-\overset{O}{\underset{\|}{S}}-O-R_2$$

wherein $R_1$ represents $C_1$–$C_{10}$ alkyl, $C_1$–$C_{10}$ hydroxyalkyl having a number of hydroxyl substituents from 1 to a value equal to the number of carbon atoms in the hydroxyalkyl group; and $R_2$ represents $C_1$–$C_{10}$ alkyl, or $C_1$–$C_{10}$ hydroxyalkyl having a number of hydroxyl substituents from 1 to a value equal to the number of carbon atoms in the hydroxyalkyl group, (B) the Formula ID:

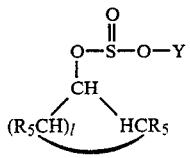
(Formula ID)

wherein
$R_5$ represents hydroxyl or

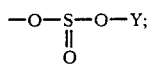

Y represents hydroxymethyl, methyl, ethyl or —(CH$_2$)$_l$—N(CH$_3$)$_3$;
l represents an integer from 1 to 4 inclusive;
t represents 1, 2 or 3, or
(C) the Formula IE:

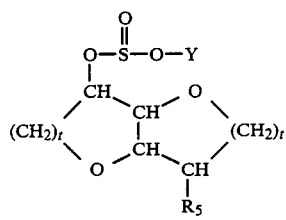
(Formula IE)

wherein
$R_5$ represents hydroxyl or

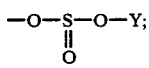

Y represents hydroxymethyl, methyl, ethyl, or —(CH$_2$)$_t$—N(CH$_3$)$_3$; and
t represents 1, 2 or 3.

2. The composition as claimed in claim 1 in which
(i) the alkyl moieties represented by $R_1$ and $R_2$ have 1 to 6 carbon atoms,
(ii) in Formula ID, l represents 4 and $R_5$ represents hydroxyl, and
(iii) in Formula IE, t represents 1 and $R_5$ represents hydroxyl.

3. A composition as claimed in claim 1, wherein the ester is diethyl sulphite.

4. A composition as claimed in claim 1 containing 50 to 500 mg of the sulfite ester per unit dose.

5. A method of treating a hypertensive or thrombotic condition in a patient in need thereof, which method comprises administering to the patient an anti-hypertensive or antithrombotic effective amount of a sulphite or bisulphite ester having:
(A) the Formula IA:

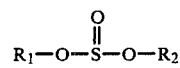
(Formula IA)

wherein
$R_1$ represents $C_1$-$C_{10}$ alkyl, $C_1$-$C_{10}$ hydroxyalkyl having a number of hydroxyl substituents from 1 to a value equal to the number of carbon atoms in the hydroxyalkyl group; and
$R_2$ represents $C_1$-$C_{10}$ alkyl, or $C_1$-$C_{10}$ hydroxylalkyl having a number of hydroxyl substituents from 1 to a value equal to the number of carbon atoms in the hydroxyalkyl group,
(B) the Formula ID:

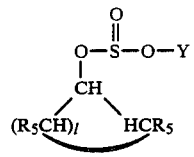
(Formula ID)

wherein
$R_5$ represents hydroxyl or

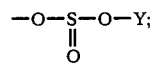

Y represents hydroxymethyl, methyl, ethyl or —(CH$_2$)$_l$—N(CH$_3$)$_3$;
l represents an integer from 1 to 4 inclusive;
t represents 1, 2 or 3, or
(C) the Formula IE:

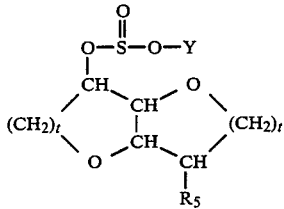
(Formula IE)

wherein
$R_5$ represents hydroxyl or

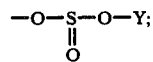

Y represents hydroxymethyl, methyl, ethyl, or —(CH$_2$)$_t$—N(CH$_3$)$_3$; and
t represents 1, 2 or 3.

6. A method as claimed in claim 5 in which the ester is diethyl sulphite.

7. A method as claimed in claim 5 in which the amount administered is from 50 to 1000 mg per dose.

8. A method as claimed in claim 7 in which the amount administered is from 50 to 500 mg per dose.

* * * * *